United States Patent [19]

Rogier

[11] 4,328,371

[45] May 4, 1982

[54] ALKYLENE OXIDE ADDUCTS OF AMINO ALCOHOLS

[75] Inventor: Edgar R. Rogier, Minnetonka, Minn.

[73] Assignee: Henkel Corporation, Minneapolis, Minn.

[21] Appl. No.: 216,212

[22] Filed: Dec. 15, 1980

[51] Int. Cl.$^3$ .............................................. C07C 91/10
[52] U.S. Cl. ..................................... 564/506; 528/77; 528/78; 528/85
[58] Field of Search ................................ 564/506, 503

[56] References Cited

U.S. PATENT DOCUMENTS

| | | | |
|---|---|---|---|
| 3,317,505 | 5/1967 | Braus | 564/506 X |
| 3,365,435 | 1/1968 | Adams et al. | 564/506 X |
| 3,697,423 | 10/1972 | Sundby et al. | 564/506 X |
| 3,872,116 | 3/1975 | Gipson | 564/506 X |

FOREIGN PATENT DOCUMENTS 1220438 7/1966 Fed. Rep. of Germany ...... 564/506

*Primary Examiner*—John Doll
*Attorney, Agent, or Firm*—Forrest L. Collins; Patrick J. Span

[57] ABSTRACT

Tertiary amino polyols are formed by reacting an amino alcohol with an alkylene oxide material.

10 Claims, No Drawings

ALKYLENE OXIDE ADDUCTS OF AMINO ALCOHOLS

BACKGROUND OF THE INVENTION

1. Field of the Invention

This invention relates to compounds which contain multiple hydroxyl groups and tertiary amine functionality.

2. Description of the Art Practices

It has recently been determined that high molecular weight alcohols may be prepared which are liquid in nature. Such materials are described in the U.S. Pat. No. 4,216,343 dated Aug. 5, 1980 also to the present author. It has been determined by the author that certain derivatives leading to the starting material of such alcohols may be valuably converted to amino alcohols which may thereafter be derivatized to amino alcohols and thereafter to an alkylene oxide adduct of the amino alcohol. Such materials are particularly valuable in that they contain both hydroxyl groups and tertiary amine functionality. The tertiary amine functionality is valuable in that it provides an autocatalytic reactant for urethane formation.

Certain work has also been done by R. Lai in an article entitled *Obtention De Derives Bio Functionnels* at Rev. Fr. Corps. Gras. 17:455 (1970). Therein, certain derivatives of alcohols are suggested.

Throughout the specification and claims, percentages and ratios are by weight and temperatures are in degrees Celsius unless otherwise indicated.

SUMMARY OF THE INVENTION

This invention describes tertiary amino polyols of the following structure:

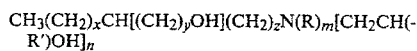

$$CH_3(CH_2)_xCH[(CH_2)_yOH](CH_2)_zN(R)_m[CH_2CH(R')OH]_n$$

and mixtures thereof; wherein the sum of the non-zero integers x plus y plus z is from 15 through 21; y plus z are greater than or equal to 3; n is 1 or 2 and the sum of m plus n is 2; R' is H or CH$_3$; and R is an alkyl group preferably having from 1 through 4 carbon atoms.

DETAILED DESCRIPTION OF THE INVENTION

It will be apparent that more than one starting material may be utilized to obtain the compounds of the present invention. Conveniently, an unsaturated alcohol, such as oleyl alcohol, may be hydroformylated to give a material which has a terminal hydroxyl functionality from the starting alcohol and a formyl group located toward the center of the molecule. A reductive amination is then conducted on such a material utilizing ammonia and hydrogen to convert the formyl group to a primary amine structure. Thereafter, this new primary amine is converted via an alkylene oxide such as ethylene oxide or propylene oxide to the N,N-bis(hydroxyalkyl) substituted amino alcohol.

Thus, starting with oleyl alcohol, one would first obtain 9(10) formyloctadecanol. This material is then converted through the reductive amination to 9(10)-aminomethyloctadecanol. The 9(10)-aminomethyloctadecanol when reacted with the ethylene oxide, then gives 9(10)-N,N-bis(2-hydroxyethyl) octadecanol. Any unsaturated linear primary alcohol having from 12 to 20 carbon atoms may be utilized to obtain the compounds of the present invention. It is also possible to use polyunsaturated linear primary alcohols, particularly when utilizing cobalt as a catalyst as the hydroformylation reaction has been observed to produce only a monoformyl derivative while reducing any additional unsaturation in the molecule. Thus, linoleyl or linolenyl alcohol only yields monoformyloctadecanol which is then derivatized as disclosed above.

An additional starting material which may be utilized to obtain compounds within the scope of the present invention is an unsaturated nitrile such as oleonitrile. In this case, the hydroformylation reaction proceeds with carbon monoxide and hydrogen gas to give 9(10) formyloctadecanonitrile. This formyl compound is then reduced with hydrogen conveniently using a hydrogenation catalyst to give 9(10)-hydroxymethyloctadecylamine. This latter amine is then reacted as described above with ethylene or propylene oxide to give 9(10)-hydroxymethyl-N,N-bis(2-hydroxyalkyl) octadecylamine.

The compounds as described above are particularly useful in that a tertiary amine group is present in the molecule which causes the compound to be autocatalytic when utilized in urethane compositions. That is, the tertiary amine group in the molecule catalyzes the urethane reaction while the hydroxyl group is reactive. Thus, the compounds of the present invention are useful as reactants with polyisocyanates, particularily for reaction injection molding applications where a fast reaction is required. It is also noted that the compounds of the present invention being autocatalytic reduce or eliminate the need for additional catalysts. Such other catalysts are undesired in some particular applications in which the compounds of the present invention are utilized.

In the structural formula given in the Summary, the sum of the integers x plus y plus z is preferably from 16 to 20, and x, y, and z are each preferably 2, 3, 4 or greater. Among the various products of this invention are:

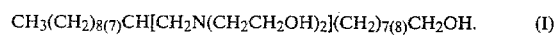

$$CH_3(CH_2)_{8(7)}CH[CH_2N(CH_2CH_2OH)_2](CH_2)_{7(8)}CH_2OH. \quad (I)$$

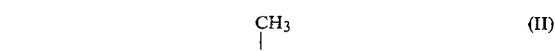

$$CH_3(CH_2)_{8(7)}CH[CH_2N(CH_2CHOH)_2](CH_2)_{7(8)}CH_2OH \overset{CH_3}{|} \quad (II)$$

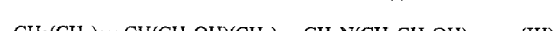

$$CH_3(CH_2)_{8(7)}CH(CH_2OH)(CH_2)_{7(8)}CH_2N(CH_2CH_2OH)_2 \quad (III)$$

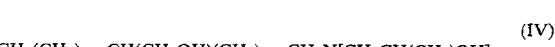

$$CH_3(CH_2)_{8(7)}CH(CH_2OH)(CH_2)_{7(8)}CH_2N[CH_2CH(CH_3)OH]_2 \quad (IV)$$

Higher alkylene oxide derivatives may also be obtained from the tertiary amino polyols. That is, the alkylene oxide adducts are formed from any of the hydroxyl groups.

The following are examples of the preparation of the compounds of the present invention.

EXAMPLE I

The manufacture of the formyloctadecanol used in the present invention is accomplished by charging a 1 liter Magne Drive, 316 SS autoclave with 606 grams (2.26 moles) of oleyl alcohol, 3.01 grams of 5 percent rhodium on alumina and 3 grams (9.68 moles) of triphenylphosphite.

The autoclave is sealed and pressurized to 10 atmospheres with nitrogen under stirring and then vented to atmospheric pressure. The nitrogen purge is repeated twice more to ensure removal of any oxygen present in the autoclave.

The autoclave is then pressurized with premixed carbon monoxide and hydrogen gas in a 1:1 molar ratio to 68 atmospheres at which point heating is started. Stirring is manually controlled at 1250 rpm and the uptake of the mixture of the gases starts at about 100 degrees C.

The reaction conditions are then maintained at a temperature of 130 degrees C. and the gas pressure at 70 to 75 atmospheres.

The reaction is substantially complete after 4.6 hours and is determined by the cessation of the gas uptake. The confirmation of completeness of the reaction is obtained by sampling the mixture and determining through gas chromatograph analysis that there is less than 1 percent of the starting alcohol in the mixture.

The reaction mixture is then cooled to 75 degrees C. vented to atmospheric pressure and purged twice with nitrogen. The contents of the autoclave are then discharged at 75 degrees C. under nitrogen pressure through a pressure filter. The yield of the formyloctadecanol is greater than 90 percent.

The reaction may be modified by using triphenylphosphine in place of the triphenylphosphite. Alternatively the oleyl alcohol may be substituted by linoleyl or linolenyl alcohol. The reaction temperature may also be lowered to 90 degrees C. at which point the reaction takes a substantially longer period of time to proceed. As a second alternative, the reaction temperature can be raised to about 150 degrees C. and the reaction time considerably lowered. However, some decomposition of the end product may occur at the higher temperatures.

In similar fashion, the mixture of carbon monoxide and hydrogen may be varied as previously described in the Detailed Description of the Invention and may also be varied between about 20 and 500 atmospheres of pressure. The lower end of the pressure range, of course, slows the reaction rate down while the higher pressure condition increases the reaction rate.

EXAMPLE II

9(10) aminomethyloctadecanol is prepared utilizing the formyloctadecanol of the foregoing example.

Into a one liter 316 SS autoclave equipped with a stirrer, thermocouple and an inlet connected to a positive displacement metering pump are charged 150 grams of absolute ethanol and 30 grams of water-wet Raney nickel.

The autoclave is flushed with nitrogen and sealed. Liquid ammonia in the amount of 150 grams is added to the autoclave using a nitrogen head. The autoclave is then heated to 130 degrees C. resulting in a pressure of 50 atmospheres absolute. The pressure in the system is increased to 61 atmospheres absolute using hydrogen.

The metering pump is then charged with 301 grams of the formyloctadecanol obtained from the preceding example. The formyloctadecanol is pumped into the autoclave with stirring over a period of 24 minutes during which time the temperature is controlled to the range of about 128 to 132 degrees C. and the pressure is controlled at from about 57 to about 61 atmospheres absolute. The reaction process is then maintained under the above conditions for an additional two hours after the addition of the formyloctadecanol is complete. The autoclave is then cooled, vented and the product discharged through a filter using nitrogen pressure. The product is stripped of solvent at about 65 degrees C. under a vacuum of less than one torr.

The yield of aminomethyloctadecanol is 292 grams having the following analysis. Hydroxyl equivalent weight: 154. Total amine equivalent. weight: 351. Secondary plus tertiary amine: 12 meq/kg.

EXAMPLE III

The preparation of N,N-bis(2-hydroxyethyl)aminomethyloctadecanol is as described below.

A 1 liter autoclave equipped with stirrer, ethylene oxide inlet system, sampling tube and thermocouple is first obtained. Into the autoclave is introduced 452 grams of the aminomethyloctadecanol of Example II.

The autoclave is sealed and flushed with nitrogen three times to, in effect, exclude all oxygen from the reaction mixture. The reaction mass in the autoclave is heated to about 52 degrees Centigrade and the ethylene oxide is slowly added over a period of approximately 2½ hours. The temperature is maintained between 52 and 63 degrees Centigrade by cooling during the addition of the ethylene oxide. After addition of the ethylene oxide is complete the temperature is maintained at from 54–61 degrees Centigrade for an additional 1.5 hours.

The reaction vessel is then cooled to 32 degrees and allowed to stand for approximately 16 hours. The reaction is then vented to the atmosphere and the product stripped of volatiles under high vacuum at 70 degrees and less than 1 torr. The yield is observed to be 527 grams having an acetylation equivalent weight of 136 and the total amine equivalent weight of 435. This reaction product corresponds to the theoretical 9(10)N,N-bis(2-hydroxyethyl) aminomethyloctadecanol.

Shown in Table I on the next page is additional information concerning the preparation of 9(10)N,N-bis(2-hydroxyethyl)aminomethyloctadecanol.

Substantially similar results are obtained when propylene oxide is employed in place of ethylene oxide.

TABLE I

| PREPARATION OF N,N-BIS(2-HYDROXYETHYL) AMINOMETHYLOCTADECANOL | | | | | | |
|---|---|---|---|---|---|---|
| AMINO ALCOHOL g(moles) | ETHYLENE OXIDE g(moles) | Temp °C. | Reaction Time (hrs) | Yield (g) | OH Eq Wt | Total |
| 267 (0.89) | 104 (2.36) | 39–60 | 10 | 303 | 142 | 462 |
| 454 | 121 (2.75) | 45–55 | 8.0 | 546 | 138 | 460 |
| 452 | 121 | 52–63 | 4.0 | 527 | 136 | 435 |
| 438 | 115 (2.61) | 45–61 | 5.0 | 523 | 134 | 436 |

EXAMPLE IV

The compounds of this example are prepared by obtaining 9(10)-formyloctadecylnitrile which is reduced per R. Lai to 9(10) hydroxymethyloctadecylnitrile using hydrogen and a hydrogenation catalyst (e.g. Ni or Co). Lai then discloses the production of 9(10)-hydroxymethyloctadecylamine from the nitrile.

The 9(10)-hydroxymethyloctadecylamine material is then reacted with two moles of propylene oxide according to the previous examples to obtain 9(10)-hydroxymethyl-N,N-bis(2-hydroxymethylpropyl)octadecylamine. Additional propylene oxide may be used to form higher alkylene oxide condensates.

EXAMPLE V

Cast elastomers products are formulated utilizing N,N-bis(2-hydroxyethyl)aminomethyloctadecanol.

Such products are formulated according to Table II shown below.

TABLE II

| Component | Product A* | Product B* |
|---|---|---|
| N,N-bis(2-hydroxyethyl)-aminoethyloctadecanol | 3/11.5 | 3/11.5 |
| Multranol 9151 (polyol from Mobay) | —/— | 0.5/31.5 |
| Niax 31-28 (polyol from Union Carbide) | 0.5/31.5 | —/— |
| 1,4-Butanediol | 5.0/7.0 | 5.0/7.0 |
| Mondur PF (polyisocyanate-Mobay) | 8.5/48.0 | 8.5/48.0 |
| Freon 11B (foaming agent) | —/2.0 | —/2.0 |
| Catalyst T-12 (DBTDL) | —/0.005 | —/0.005 |
| Setting Time Min. | 1.0 | 1.5 |
| Demolding time Min. | 2.0 | 3.0 |
| Curing time, Hr. 120° C. | 1.0 | 1.0 |

*The first figure in each category is the number of equivalent and the second figure is the percentage by weight in the composition.

The above products may also be used for RIM.

The procedure for manufacturing the cast elastomers of the present invention are as follows: The hydroxyl components are combined, demoisturized and degassed at 60 degrees C. under a vacuum. The equivalent amount of the isocyanate, the foaming agent and urethane catalyst are added to the hydroxyl components. The contents of the elastomers formulation are stirred for 20 seconds then poured into a preheated mold and a press having a 4545 kilogram load is applied. The elastomer is allowed to set which occurs in about one minute. The elastomer is then demolded and placed in an oven at 120 degrees C. for one hour for final curing.

Product A and Product B are evaluated below in Table III. Product A and Product B may also be used for reaction injection molding (RIM) compositions.

TABLE III

| PHYSICAL PROPERTIES OF ELASTOMERS AT −20° F. | | |
|---|---|---|
| | PRODUCT A | PRODUCT B |
| Shore A at room temp. | 73 | 73 |
| Tensile strength, psi at −20° F. | 5,500 | 11,834 |
| Elongation, % at −20° F. | 0 | 0 |
| Elongation set, % at −20° F. | 0 | 0 |
| Modulus of elasticity in bending, psi, at −20° F. | 230,790 | 326,797 |

What is claimed is:

1. Tertiary amino polyols of the following structure:

$$CH_3(CH_2)_xCH[(CH_2)_yOH](CH_2)_zN(R)_m[CH_2CH(R')OH]_n$$

and mixtures thereof; wherein the sum of the non-zero integers x plus y plus z is from 15 through 21; y plus z are greater than or equal to 3; n is 1 or 2 and the sum of m plus n is 2; R' is H or CH$_3$; and R is an alkyl group.

2. The tertiary amino polyol of claim 1 wherein x, y, and z are each 2 or greater.

3. The tertiary amino polyol of claim 1 wherein the sum of x plus y plus z is from 16 through 20.

4. The tertiary amino polyol of claim 1 where R has from 1 to 4 carbon atoms.

5. The tertiary amino polyol of claim 1 wherein R' is H.

6. The tertiary amino polyol of claim 1 which is $$CH_3(CH_2)_{8(7)}CH[CH_2N(CH_2CH_2OH)_2](CH_2)_{7(8)}CH_2OH.$$

7. The tertiary amino polyol of claim 1 which is $$CH_3(CH_2)_{8(7)}CH[CH_2N(CH_2\overset{\underset{\displaystyle CH_3}{|}}{C}HOH)_2](CH_2)_{7(8)}CH_2OH.$$

8. The tertiary amino polyol of claim 1 which is $$CH_3(CH_2)_{8(7)}CH(CH_2OH)(CH_2)_{7(8)}CH_2N(CH_2CH_2OH)_2.$$

9. The tertiary amino polyol of claim 1 which is $$CH_3(CH_2)_{8(7)}CH(CH_2OH)(CH_2)_{7(8)}CH_2N[CH_2CH(CH_3)OH]_2.$$

10. The tertiary amino polyol of claim 1 wherein z is 4 or greater.

* * * * *